United States Patent
Engqvist et al.

(10) Patent No.: US 10,632,231 B2
(45) Date of Patent: Apr. 28, 2020

(54) METHODS OF FORMING A POROUS CERAMIC SHAPED ARTICLE AND POROUS CERAMIC PRODUCTS

(71) Applicant: OssDsign AB, Uppsala (SE)

(72) Inventors: Håkan Engqvist, Östhammar (SE); Johanna Unosson, Uppsala (SE)

(73) Assignee: OSSDSIGN AB, Uppsala (SE)

( * ) Notice: Subject to any disclaimer, the term of this patent is extended or adjusted under 35 U.S.C. 154(b) by 0 days.

(21) Appl. No.: 15/305,010

(22) PCT Filed: Apr. 24, 2015

(86) PCT No.: PCT/IB2015/053009
§ 371 (c)(1),
(2) Date: Oct. 18, 2016

(87) PCT Pub. No.: WO2015/162597
PCT Pub. Date: Oct. 29, 2015

(65) Prior Publication Data
US 2017/0151371 A1    Jun. 1, 2017

(30) Foreign Application Priority Data
Apr. 24, 2014 (SE) ...................................... 1400213

(51) Int. Cl.
*A61L 27/56* (2006.01)
*A61L 27/10* (2006.01)
(Continued)

(52) U.S. Cl.
CPC .............. *A61L 27/56* (2013.01); *A61L 27/10* (2013.01); *A61L 27/12* (2013.01); *A61L 27/18* (2013.01);
(Continued)

(58) Field of Classification Search
None
See application file for complete search history.

(56) References Cited

U.S. PATENT DOCUMENTS 4,083,906 A * 4/1978 Schindler ................... C08J 9/28
264/49
4,777,153 A    10/1988 Sonuparlak et al.
(Continued)

FOREIGN PATENT DOCUMENTS

EP      1380313 A1    1/2004
WO   2009/110917 A1   9/2009
(Continued)

OTHER PUBLICATIONS

Tamimi et al., "Review: Dicalcium phosphate cements: Brushite and monetite", Acta Biomaterialia 8, pp. 474-487 (2012).*
Xu et al, Biomaterials, 27:4279-4287 (2006).

*Primary Examiner* — Bethany P Barham
*Assistant Examiner* — Barbara S Frazier
(74) *Attorney, Agent, or Firm* — Porter Wright Morris & Arthur LLP

(57) ABSTRACT

A method for making a porous, chemically bonded ceramic shaped article comprises i) providing a precursor powder mixture comprising polymer particles and a ceramic self-setting cementitious powder; ii) preparing a shaped article from a paste comprising the precursor powder mixture and an aqueous liquid; and iii) immersing the shaped article in an immersing liquid in which the polymer particles are soluble, for a period of time of from about 10 minutes to about two weeks to dissolve the polymer particles in the immersing liquid, thereby creating pores in the shaped article. A porous, chemically bonded ceramic shaped article having interconnected pores, a total porosity of at least about 50%, and a macroporosity of at least about 30% can be formed by such methods.

25 Claims, 2 Drawing Sheets

(51) Int. Cl.
    *A61L 27/12*         (2006.01)
    *A61L 27/18*         (2006.01)
    *A61L 27/54*         (2006.01)
    *A61L 27/58*         (2006.01)
    *C04B 24/32*         (2006.01)
    *C04B 28/14*         (2006.01)
    *C04B 28/18*         (2006.01)
    *C04B 28/34*         (2006.01)
    *C04B 38/04*         (2006.01)
    *C04B 111/00*        (2006.01)

(52) U.S. Cl.
    CPC ............... *A61L 27/54* (2013.01); *A61L 27/58* (2013.01); *C04B 28/14* (2013.01); *C04B 28/188* (2013.01); *C04B 28/34* (2013.01); *C04B 28/344* (2013.01); *A61L 2300/64* (2013.01); *C04B 2111/00836* (2013.01)

(56) References Cited

U.S. PATENT DOCUMENTS

| | | | |
|---|---|---|---|
| 5,702,716 | A * | 12/1997 | Dunn ................... A61K 9/0024 |
| | | | 424/422 |
| 6,949,251 | B2 | 9/2005 | Dalal et al. |
| 7,163,651 | B2 | 1/2007 | Chern Lin et al. |
| 7,357,941 | B2 | 4/2008 | Dalal et al. |
| 7,390,498 | B2 | 6/2008 | Dalal et al. |
| 8,071,156 | B2 | 12/2011 | Weber et al. |
| 8,173,149 | B2 | 5/2012 | Dalal et al. |
| 2012/0093771 | A1 | 4/2012 | Lin et al. |
| 2012/0115780 | A1 | 5/2012 | Delaney et al. |

FOREIGN PATENT DOCUMENTS

| | | |
|---|---|---|
| WO | 2012/045013 A2 | 4/2012 |
| WO | 2013/096831 A1 | 6/2013 |

* cited by examiner

METHODS OF FORMING A POROUS CERAMIC SHAPED ARTICLE AND POROUS CERAMIC PRODUCTS

FIELD OF THE INVENTION

The present invention is directed to methods of forming porous ceramic shaped articles and, more specifically, the invention relates to methods of forming porous ceramic shaped articles using a sacrifying phase. The invention is also directed to porous ceramic shaped articles which, in one embodiment, are particularly advantageous for use in biomedical applications, for example as implants and scaffolds for drug and cell delivery in vivo. In certain embodiments, the porous ceramic shaped articles are macroporous, and in certain embodiments, the porous shaped articles have a uniform porosity.

BACKGROUND OF THE INVENTION

Synthetic materials intended for bone void filling have been a topic of research interest for several years and there are many potential and important applications for such materials, including, among others, the filling of voids due to osteosarcoma and trauma. The gold standard in practice today, autologous bone, has disadvantages in its limited availability and in the risk of resistant pain. To overcome such drawbacks associated with the use of autologous bone, synthetic materials have become an important substitute. Calcium phosphate ceramics are one of the main groups of synthetic materials used in these applications and they advantageously combine biodegradation and biocompatibility. The calcium phosphate ceramics have the advantage of a chemical composition similar to the mineral phase of bone, i.e., ion-substituted calcium-deficient hydroxyapatite.

Calcium phosphate (CaP) materials for bone void filling applications are provided in many physical forms including premade scaffolds, granules, putties and self-setting cements. CaPs that are produced through a low temperature method, i.e., through a cement dissolution-precipitation reaction, are known as chemically bonded ceramic materials and have an entangled network of small crystallites. The small size of the crystallites makes the calcium phosphate cements (CPCs) degrade more rapidly than scaffolds prepared through a high temperature sintering process where larger and more compact crystals are formed.

It is highly desirable for a bone void-filling material to have a fast resorption rate, mirroring an equally fast formation of new bone. Resorbable CaP implants should work as a template for new bone formation and prevent the formation of fibrotic tissue within a bone void, rather than being a permanent bone substitute, similar to the manner in which autologous bone functions. To increase the bone ingrowth in synthetic bone void fillers, it has been suggested, and tested with good results, that the introduction of macropores could be helpful. Two main mechanisms are responsible for the bone ingrowth into bone void fillers. The first is osteoclastic degradation, similar to the normal remodelling mechanism of bone, and the second is resorption through dissolution of the material. Although the CPC based bone void fillers have a high inherent porosity, the pore size mainly lies in the vicinity of 1 µm and lower. An increased amount of macropores, i.e., pores having a size greater than 10 µm, as well as an increased interconnectivity of pores, could improve the cell colonization within the material and increase the osteoclastic degradation. Studies have shown that pore sizes greater than 100 µm are required for a good bone ingrowth, while sizes greater than 300 µm are recommended to achieve enhanced capillary and bone formation. See Karageorgiou et al, *Biomaterials,* 26:5474-91 (2005).

Macroporous cements can be either injected into a bone void and set in situ or hardened outside the body into a desired shape, normally into a granule shape, and used as an in vitro scaffold or an implant. The introduction of macropores into a cement has conventionally been performed through several routes. One method employs a mixture of the cement phase with a sacrifying phase (normally a sugar), which is dissolved after cement setting, thereby creating voids. Another method incorporates a surfactant to entrap air during cement mixing (see Sarda et al, *Journal of Biomedical Materials Research Part A;* 65A:215-21 (2003). Mechanical foaming of the cement paste is also used (see Ginebra et al, *Journal of Biomedical Materials Research Part A,* 80A:351-61 (2007); Perut et al, *Acta Biomaterialia,* 7:1780-7 (2011); Montufar et al, *Journal of Materials Science: Materials in Medicine,* 21:863-9 (2010)). The two main approaches, however, are the use of a sacrifying phase and mechanical foaming. The drawback with these conventional methods is the difficulty to achieve a controlled pore size distribution and interconnectivity, i.e., interconnection of pores. Although foaming could give a controlled distribution of pores in the foam through a rigorously-controlled foaming procedure, the foams are easily ruptured and distorted during cement setting and assuring an even distribution of pores in the final product is difficult. The use of a sugar as a sacrifying phase also has several disadvantages. Mainly, the fast dissolution of the sugars often causes dissolution before the setting of the cement has started, affecting the cement setting mechanism and creating unpredictable pore sizes and distribution. The sugars are furthermore hard to mold into desired shapes, limiting the size and shape of the sacrifying phase.

Accordingly, new methods for forming porous ceramic shaped articles are needed, and, additionally, new methods for forming porous ceramic shaped articles having macropores suitable for use as implants which avoid drawbacks of the prior art are needed.

SUMMARY OF THE INVENTION

It is an object of the present invention to provide new methods for forming porous ceramic shaped articles. It is a related object to provide porous ceramic shaped articles.

In one embodiment, the invention is directed to a method for making a porous, chemically bonded ceramic shaped article. The method comprises i) providing a precursor powder mixture comprising polymer particles and a ceramic self-setting cementitious powder; ii) preparing a shaped article from a paste comprising the precursor powder mixture and an aqueous liquid; and iii) immersing the shaped article in an immersing liquid in which the polymer particles are soluble, for a period of time of from about 10 minutes to about two weeks to dissolve the polymer particles in the immersing liquid, thereby creating pores in the shaped article.

In another embodiment, the invention is directed to a porous, chemically bonded ceramic shaped article having interconnected pores, a total porosity of at least about 50%, and a macroporosity of at least about 30%.

The methods and shaped articles of the invention are advantageous in providing shaped articles with controlled porosity and, in certain embodiments, with controlled macroporosity. These and additional advantages will be more fully apparent in view of the detailed description herein.

BRIEF DESCRIPTION OF THE DRAWING

Certain aspects of the invention may be better understood when viewed in connection with the Drawing, in which.

DETAILED DESCRIPTION

Figure 1:
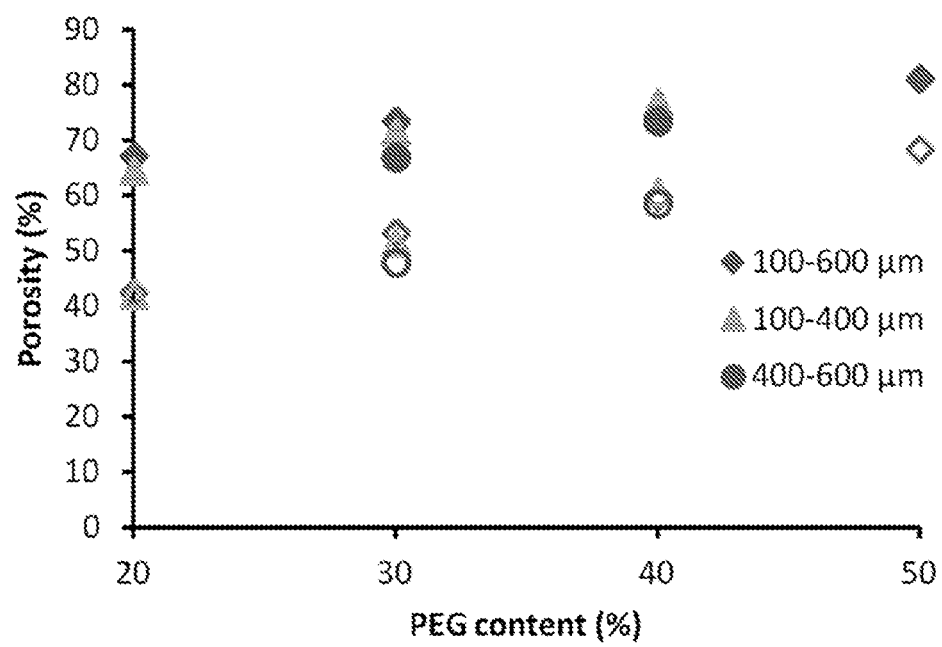
FIG. 1 shows porosity (total porosity and macroporosity) of a ceramic material as a function of polymer particle content in a precursor powder mixture, as described in Example 1. Solid markers show total porosity and hollow markers show macroporosity.

The inventive method comprises i) providing a precursor powder mixture comprising polymer particles and a ceramic self-setting cementitious powder; ii) preparing a shaped article from a paste comprising the precursor powder mixture and an aqueous liquid; and iii) immersing the shaped article in an immersing liquid in which the polymer particles are soluble, for a period of time of from about 10 minutes to about two weeks to dissolve the polymer particles in the immersing liquid, thereby creating pores in the shaped article.

The polymer which is employed is selected to be solid in the precursor powder and soluble in the immersing liquid. In a specific embodiment, the polymer is water soluble. In another specific embodiment, the polymer comprises water-soluble polyethylene glycol and, more specifically, the polymer particles comprise at least 50 wt %, 60 wt %, or 70 wt % water-soluble polyethylene glycol. In further embodiments, the polymer particles consist essentially of water-soluble polyethylene glycol, i.e., only insignificant amounts of any other polymer or other material are employed, or the polymer particles consist of water-soluble polyethylene glycol, i.e., no other polymer or other material is included in the particles. Any polymer or other material included in the polymer particles should not adversely influence the melting point of the particles, i.e., the melting point of the particles should be such that the particles are solid at room temperature and during any processing which requires a solid material to provide particles of a desired size, i.e., grinding, milling, sieving or the like. Additionally, any polymer or other material included in the polymer particles should not adversely influence the dissolution of the polymer particles in the immersing liquid beyond the parameters discussed below.

In specific embodiments, the polymer particles comprise polyethylene glycol having a molecular weight sufficiently high to ensure that the particles are solid at room temperature (20-25° C.), and more specifically, at a temperature of at least 40° C., or more specifically, 50° C., so the polymer can be ground, milled or otherwise mechanically processed to a controlled size without melting during such processing and to ensure that the precursor powder mixture can be mixed with an aqueous liquid to form the paste and the article can be shaped without significant dissolution of the polymer particles. Further, the polyethylene glycol has a molecular weight sufficiently low to ensure that the particles are sufficiently water soluble when the shaped article is immersed in the immersing liquid to obtain a reasonably fast dissolution rate in the immersing liquid in a reasonable scarifying phase removal time. In specific embodiments, the dissolution time is not shorter than about 10 minutes but not longer than about 10 weeks, more specifically, less than two weeks, one week, or one to five days, or, even more specifically, about 24 hours, particularly at a desired sacrifying phase removal temperature, i.e., in the range of 1 to 100° C., or, specifically, at room temperature. In a specific embodiment, the polymer exhibits the aforementioned dissolution time in the aforementioned sacrifying phase removal temperature when the immersing liquid is water and the immersion is conducted at atmospheric pressure. In more specific embodiments, the polyethylene glycol has a weight average molecular weight, $M_w$, in a range of from about 900 g/mol to about 100,000 g/mol, a range of from about 5000 g/mol to about 50,000 g/mol, or a range of from about 5000 g/mol to about 30 000 g/mol.

The polymer particles may exhibit a slight solubility when the precursor powder is mixed with the aqueous liquid to form the paste, but the polymer particles are substantially insoluble in the paste and until the shaped article is formed and hardened so that subsequent dissolution of the polymer particles forms an interconnected pore structure, or, in certain embodiments, an interconnected macropore structure, when immersed in the immersing liquid.

The polymer particles are selected or formed to a specified particle size, shape, and distribution in order to control the porosity in the shaped article. In specific embodiments, the polymer particles have an average particle size in a range of about 10 μm to about 1000 μm, an average particle size from about 50 to about 1000 μm, an average particle size of from about 100 μm to about 800 μm, an average particle size of from about 300 μm to about 600 μm, an average particle size of from about 100 μm to about 200 μm, or an average particle size of from about 200 μm to about 300 μm. In another embodiment, at least about 50%, 60%, 70%, 80% or 90% of the polymer particles have a size in a range of from about 10 μm to about 1000 μm, about 50 to about 1000 μm, about 100 μm to about 800 μm, about 300 μm to about 600 μm, about 100 μm to about 200 μm, or about 200 μm to about 300 μm. Polymer particles in these ranges will provide the shaped article with desirable macroporosity and interconnected pores. The polymer particles may be shaped and sized through various processes known in the art, including, but not limited to, molding, grinding, and/or sieving.

The precursor powder mixture comprises the polymer particles and a ceramic self-setting cementitious powder. A ceramic self-setting cementitious powder is one that forms a chemically bonded cement and does not require sintering. The self-setting cementitious powder can be any of, but not limited to, one or more of the following: calcium phosphates, calcium sulfates, calcium silicates (e.g. CS, C2S and/or C3S (where C=CaO and S=SiO2)), calcium carbonates (e.g. amorphous, aragonite, calcite, vaterite), magnesium carbonates, and calcium aluminates (e.g. CA, C12A7, C3A (where C=CaO and A=Al2O3)), or a mixture of two or more thereof. In specific embodiments, the powder comprises one or more calcium phosphates selected from the group consisting of anhydrous dicalcium phosphate, dicalcium phosphate dihydrate, monocalcium phosphate monohydrate, octacalcium phosphate, α-tricalcium phosphate, β-tricalcium phosphate, amorphous calcium phosphate, calcium-deficient hydroxyapatite, non-stoichiometric hydroxyapatite, and tetracalcium phosphate. The calcium phosphate powders may be selected to form Brushite, Monetite, and/or hydroxyapatite. In further embodiments, the calcium phosphate powders comprise a mixture of monocalcium phosphate monohydrate and β-tricalcium phosphate, for example, in about equimolar amounts.

As is known in the art, the cementitious powder may be selected to be acidic, neutral or basic, facilitating formation of a desired hardened cement composition. For example, an acidic cement-forming paste will form Monetite or Brushite, while a neutral or basic cement-forming paste will form hydroxyapatite.

The polymer particles function as a template for the porosity of the shaped article and, in a specific embodiment, macropores. Macropores are defined as pores having a size great than about 10 μm. In specific embodiments, the shaped article has macropores greater than about 50 μm, 100 μm, 200 μm or 300 μm. In additional embodiments, the shaped article has macropores ranging in size from about 50 μm to about 1000 μm, about 100 μm to about 800 μm, about 300 μm to about 600 μm, about 100 μm to about 200 μm, or about 200 μm to about 300 μm. Porosity size and distribution can be calculated using volume and density measurements or can be measured using micro-computed tomography as described in the Examples.

The polymer particles and the ceramic powder are mixed in desired ratios. In a specific embodiment, the precursor powder mixture comprises from about 10 to about 60 wt %, from about 20 to about 50 wt %, or from about 20 to about 40 wt %, based on the weight of the mixture, of the polymer particles, and a balance of the ceramic powder. If the polymer particle content is too low, the shaped article will not have a sufficient porosity for loading, for example, to induce cell loading, and if the polymer content is too high, the shaped article will not have sufficient mechanical strength.

An aqueous liquid is added to the precursor powder mixture to form a cement paste in which the dissolution-precipitation reaction of the ceramic cementitious powder is initiated. In a specific embodiment, the aqueous liquid is mainly water. In specific embodiments, the aqueous liquid comprises at least 50 wt %, at least 60 wt %, at least 70 wt %, at least 80 wt %, at least 90 wt % or 100 wt % water. One or more conventional additives may be included in the precursor powder mixture, the aqueous liquid used to form the paste, or the paste itself in order to influence the setting time of the cement.

The paste is shaped into a desired article, for example, granules or a custom shape. Generally, the time in which the paste may be shaped is relatively short, several minutes to less than an hour, as the aqueous liquid causes the ceramic powder to react and harden, i.e., set, although longer setting times are also encompassed within the invention.

After the ceramic has set, the polymer particles are removed by immersion of the shaped article in the immersing liquid. In a specific embodiment, the polymer particles are water soluble and the immersing liquid is water. The article is maintained in the immersing liquid until all polymer is dissolved and removed. The immersing liquid is preferably changed one or several times to ensure complete polymer removal. The time of the dissolution step is referred to as the sacrifying phase removal time and the temperature as the sacrifying phase removal temperature. In specific embodiments, at least about 50 wt %, 60 wt %, 70 wt %, 80 wt %, 90 wt %, or all of the polymer particles are dissolved in the immersing liquid within 24 hours at room temperature.

As the polymer particles are dissolved in the immersing liquid, pores are created in the shaped article. Polymer particles which are sized as described herein, used in the disclosed amounts, can provide a shaped article with interconnected macropores. Thus, the shaped article can be molded directly to its final geometry with macropores according to specific embodiments as described herein. Controlling the polymer particle size to a narrow distribution will assist in forming macropores of similarly uniform size. In specific embodiments, the ceramic shaped articles produced by the inventive methods have interconnected pores, a total porosity of at least about 50%, 60% or 70%, and a macroporosity of at least about 30%, 40% or 50%. The inventive method therefore provides an efficient way to produce controlled macroporous materials. The materials, as well as parameters such as particle sizes, and process-related parameters such as processing times and temperatures as described herein may be varied within the scope of the invention.

The resulting porous shaped article may then be removed from the immersing liquid and optionally, washed and sterilized for subsequent use. The porous shaped article is suitably used as an in vitro scaffold material or a biomedical implant. An implant optionally can be loaded with a pharmaceutical active ingredient, cells or the like for in vivo delivery. In one embodiment, the shaped article may be used as a scaffold for stem cells. In another embodiment, when the implant is used for drug delivery, macroporosity may not be required, in which case the polymer particles may have a smaller size, for example of less than 50 μm, less than 10 μm, or less than 1 μm.

EXAMPLE 1

This example demonstrates various aspects of certain embodiments of the methods and materials of the invention.

Polyethylene glycol (PEG) with a Mw of 20,000 g/mol was used, the molecular weight being low enough that the PEG dissolves quite fast in water and high enough that the PEG is solid at room temperature and slightly higher temperatures, making it possible to grind and mill the PEG without melting the polymer (Mp=63-66° C.). PEG flakes were melted at 100° C. for approximately 10 minutes, cooled, ground by hand, and sieved to desired particle sizes as described in Table 1.

Monocalcium phosphate monohydrate (MCPM) (Scharlau, CA0211005P, batch 14160301, Spain) and β-TCP (Sigma-Aldrich), were mixed in a 45:55 molar ratio together with 1 wt % disodium dihydrogen pyrophosphate (SPP, Sigma-Aldrich). The sieved PEG was added in appropriate amounts according to Table 1. Citric acid (0.5 M (aq)) was used as the liquid phase in a liquid/paste (L/P) ratio of 0.25 ml/g (not including the PEG content). The mixing was performed twice for thirty seconds in 50 mL falcon tubes, using a Cap-Vibrator (Ivoclar Vivadent, Liechtenstein). Generally 5 g of CaP powder and appropriate amount of PEG was added to the bottom of a 50 mL falcon tube and mixed in a Turbula for approximately 10 minutes. 1.25 mL of citric acid was added and the cement was mixed in the Cap-Vibrator for two periods of 30 seconds each.

The resulting paste was molded in silicon rubber molds of diameter 8 mm×height 3 mm and six samples were placed together in 50 mL of PBS at 37° C. for 24 h. The samples were then polished (both sides) and removed from the molds, and 12 samples were placed together in 90 mL of fresh PBS at 60° C. The PBS was changed once after 24-48 h and removed after another 24-48 h. The samples were dried at 60° C. for 24 hours.

TABLE 1

Compositions

| | PEG size | PEG (eq, wt) | Calcium phosphate (eq, wt) | L/P (ml/g) |
|---|---|---|---|---|
| 1 | 100-600 µm | 0.6 | 1 | 0.25 |
| 2 | 100-600 µm | 0.4 | 1 | 0.25 |
| 3 | 100-400 µm | 0.6 | 1 | 0.25 |
| 4 | 100-400 µm | 0.4 | 1 | 0.25 |
| 5 | 100-600 µm | 0.8 | 1 | 0.25 |
| 6 | 100-600 µm | 1 | 1 | 0.25 |
| 7 | 100-400 µm | 0.8 | 1 | 0.25 |
| 8 | 400-600 µm | 0.8 | 1 | 0.25 |
| 9 | 400-600 µm | 0.6 | 1 | 0.25 |
| 10 | NA | 0 | 1 | 0.25 |

The apparent density of the resulting porous samples ($\rho_{a,p}$) was measured by using a caliper to estimate the apparent volume of the samples and by weighing the samples after drying. The skeletal density ($\rho_s$) was measured using helium pycnometry. The total porosity was then calculated with the following equation $$\Phi_{tot}(\%) = \left(1 - \frac{\rho_{a,p}}{\rho_s}\right) \cdot 100$$

Macroporosity was calculated according to Takagi et al, *Journal of Materials Science Materials in Medicine*, 12:135-9 (2001), using the apparent density of the sample without PEG ($\rho_{a,np}$), according to the equation below:

$$\Phi_{macro}(\%) = \left(1 - \frac{\rho_{a,p}}{\rho_{a,np}}\right) \cdot 100$$

The results are presented in Table 2.

TABLE 2

Results from measurement of porosity

| PEG size | PEG (%) | total porosity (%) | stdev | Macroporosity (%) | stdev |
|---|---|---|---|---|---|
| 100-600 µm | 20 | 67.1 | 0.7 | 42.4 | 1.3 |
| 100-600 µm | 30 | 73.5 | 0.7 | 53.3 | 1.3 |
| 100-600 µm | 40 | 74.8 | 0.9 | 59.8 | 1.4 |
| 100-600 µm | 50 | 81.2 | 0.8 | 68.4 | 1.3 |
| 100-400 µm | 20 | 64.5 | 1.1 | 42 | 1.8 |
| 100-400 µm | 30 | 71.7 | 0.5 | 51.6 | 0.9 |
| 100-400 µm | 40 | 77 | 0.9 | 60.6 | 1.5 |
| 400-600 µm | 30 | 66.9 | 0.6 | 47.9 | 0.9 |
| 400-600 µm | 40 | 73.5 | 0.9 | 58.5 | 1.5 |

This example shows that the present methods can be used to efficiently produce cements having controlled macroporosity.

EXAMPLE 2

This example demonstrates various aspects of certain embodiments of the methods and materials of the invention.

Poly(ethylene glycol) PEG (20 000 g/mol, aaa, Sigma Aldrich, Germany) was melted at 70° C., crushed and sieved to between 100 and 600 µm. Three grams of the sieved PEG was mixed with 0.060 g β-TCP and 1.940 g α-TCP. The powders were mixed in a Turbula (Willy A Bachofen AG, Switzerland) for 1 hour before the liquid (0.8 mL 2.5% Na$_2$HPO$_4$ (aq)) was added. The paste was mixed for 1 minute using a CapVibrator (Ivoclar Vivadent, USA) and molded in Teflon molds with a diameter of 1.2 mm and a height of 1.2 mm and left to cure at room temperature (21° C.) for 48 hours. The formed granules were then demolded. The PEG was removed from the granules by first washing the granules four times with 100 mL water, after which an additional 100 mL was added and the granules were stored for 2 hours at 70° C. The water was changed and the granules were stored again in 100 mL water for 2 hours at 70° C. After complete removal of the sacrificial phase (i.e. PEG) the granules were dried at 70° C. for 48 hours. Thermogravimetric analysis was performed on the dried granules to ensure complete removal of the PEG.

Figure 2:
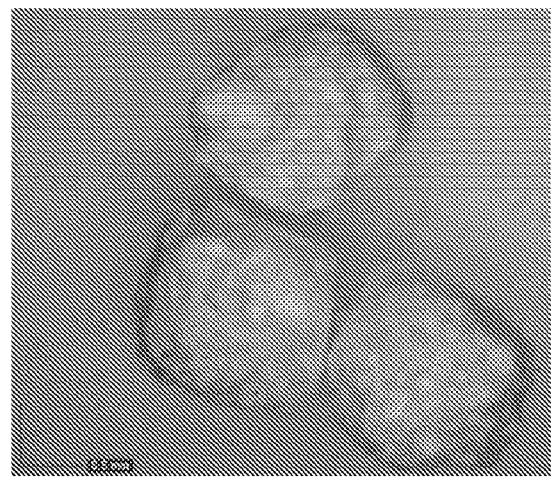
FIG. 2 shows an optical image of granules produced in Example 2.
Figure 3:
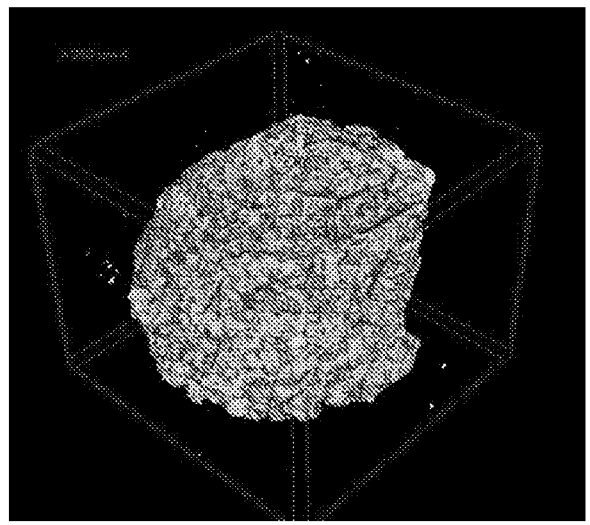
FIG. 3 shows a micro-computed tomography (μCT) image of a granule produced in Example 2.
Figure 4:
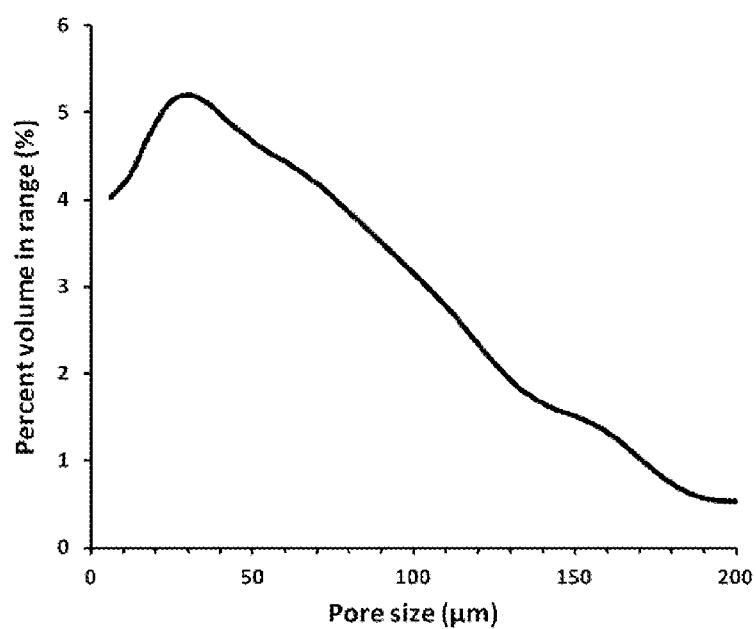
FIG. 4 shows the pore volume and distribution of granules produced in Example 2.

The calcium phosphate granules have a diameter between 1.0 and 1.2 mm and a height of 1.2 to 1.6 mm (FIGS. 2 and 3). The granules have a total porosity of approximately 75% and a macroporosity of approximately 45%. The macropore size is between 10 and 200 µm, with the average at approximately 80 µm. The pore size distribution from µCT measurements is shown in FIG. 4. The crystal composition of the granules was a mixture of calcium deficient hydroxyapatite with less than 10% β-TCP and α-TCP.

The specific embodiments and examples described herein are exemplary only in nature and are not intended to be limiting of the invention defined by the claims. Further embodiments and examples, and advantages thereof, will be apparent to one of ordinary skill in the art in view of this specification and are within the scope of the claimed invention.

What is claimed is:

1. A method for making a chemically bonded ceramic shaped article having interconnected macropores, comprising:
    i) providing a precursor powder mixture comprising macropore-forming particles consisting of water-soluble polyethylene glycol, and a ceramic self-setting cementitious powder, wherein (i) the polyethylene glycol has a weight average molecular weight, Mw, in a range of from about 5000 g/mol to about 30,000 g/mol and the macropore-forming particles have an average particle size of from about 100 µm to about 800 µm, and (ii) the ceramic self-setting cementitious powder comprises at least one calcium phosphate powder;
    ii) preparing a shaped article comprising monetite, brushite, or hydroxyapatite from a paste comprising the precursor powder mixture and an aqueous liquid;
    iii) immersing the shaped article in an immersing liquid in which the macropore-forming particles are soluble, for a period of time of from about 10 minutes to about two weeks to dissolve the macropore-forming particles in the immersing liquid, thereby creating interconnected macropores in the shaped article, wherein the macropore-forming particles are sufficiently insoluble in the paste that subsequent dissolution of the macropore-forming particles in the immersing liquid creates the interconnected macropores in the shaped article.

2. The method according to claim 1, wherein the macropore-forming particles have an average particle size of from about 100 μm to about 600 μm.

3. The method according to claim 1, wherein the precursor powder mixture comprises from about 10 to about 60 wt % of the macropore-forming particles.

4. The method according to claim 1, wherein the shaped article comprises granules.

5. The method according to claim 1, wherein a shaped article comprising Brushite is formed.

6. The method according to claim 1, wherein a shaped article comprising Monetite is formed.

7. The method according to claim 1, wherein the immersing liquid comprises water.

8. The method according to claim 1, wherein at least about 80 wt % of the macropore-forming particles are dissolved in the immersing liquid within 24 hours.

9. The method according to claim 1, wherein the precursor powder mixture comprises from about 20 to about 50 wt % of the macropore-forming particles.

10. The method according to claim 1, wherein the precursor powder mixture comprises from about 20 to about 40 wt % of the macropore-forming particles.

11. The method according to claim 1, wherein the macropore-forming particles have an average particle size of from about 300 μm to about 600 μm.

12. The method according to claim 1, wherein the macropore-forming particles have an average particle size of from about 100 μm to about 200 μm.

13. The method according to claim 1, wherein the macropore-forming particles have an average particle size of from about 200 μm to about 300 μm.

14. The method according to claim 1, wherein at least about 90 wt % of the macropore-forming particles are dissolved in the immersing liquid within 24 hours.

15. The method according to claim 1, wherein all of the macropore-forming particles are dissolved in the immersing liquid within 24 hours.

16. The method according to claim 1, wherein the resulting porous, chemically bonded ceramic shaped article has a total porosity of at least about 50%, based on the volume of the shaped article, and a macroporosity of at least about 30%, based on the volume of the shaped article.

17. The method according to claim 1, wherein a pharmaceutically active agent for in vivo delivery is loaded into pores of the resulting macroporous ceramic shaped article.

18. The method according to claim 1, wherein cells for in vivo delivery are loaded into pores of the resulting macroporous ceramic shaped article.

19. The method according to claim 1, wherein a shaped article comprising hydroxyapatite is formed.

20. The method of claim 1, wherein the ceramic self-setting cementitious powder comprises a mixture of monocalcium phosphate monohydrate and β-tricalcium phosphate.

21. A method for making a chemically bonded ceramic shaped article having interconnected macropores, comprising:
i) providing a precursor powder mixture comprising macropore-forming particles consisting essentially of water-soluble polyethylene glycol, and a ceramic self-setting cementitious powder, wherein the polyethylene glycol has a weight average molecular weight, Mw, in a range of from about 5000 g/mol to about 30,000 g/mol and the macropore-forming particles have an average particle size of from about 100 μm to about 800 μm, and wherein the ceramic self-setting cementitious powder comprises a mixture of monocalcium phosphate monohydrate and β-tricalcium phosphate;
ii) preparing a shaped article comprising monetite from a paste comprising the precursor powder mixture and an aqueous liquid;
iii) immersing the shaped article in an immersing liquid in which the macropore-forming particles are soluble to dissolve at least 80 wt % of the macropore-forming particles in the immersing liquid within 24 hours, wherein the macropore-forming particles are sufficiently insoluble in the paste that subsequent dissolution of the macropore-forming particles in the immersing liquid creates interconnected macropores in the shaped article, wherein the shaped article comprises interconnected macropores.

22. The method according to claim 21, wherein said macropore-forming particles consist of water-soluble polyethylene glycol.

23. The method according to claim 21, wherein the precursor powder mixture comprises from about 20 to about 50 wt % of the macropore-forming particles.

24. The method according to claim 21, wherein the resulting porous, chemically bonded ceramic shaped article has a total porosity of at least about 50%, based on the volume of the shaped article, and a macroporosity of at least about 30%, based on the volume of the shaped article.

25. The method according to claim 21, wherein cells for in vivo delivery are loaded into pores of the resulting macroporous ceramic shaped article.

* * * * *

UNITED STATES PATENT AND TRADEMARK OFFICE
CERTIFICATE OF CORRECTION

PATENT NO. : 10,632,231 B2
APPLICATION NO. : 15/305010
DATED : April 28, 2020
INVENTOR(S) : Håkan Engqvist et al.

Page 1 of 1

It is certified that error appears in the above-identified patent and that said Letters Patent is hereby corrected as shown below:

On the Title Page

Item (30), change "1400213" to --1400213-3--.

Signed and Sealed this
Eighteenth Day of August, 2020

Andrei Iancu
*Director of the United States Patent and Trademark Office*